United States Patent [19]

Diamantoglou

[11] Patent Number: 4,962,140

[45] Date of Patent: Oct. 9, 1990

[54] PROCESS FOR PRODUCING CELLULOSIC DIALYSIS MEMBRANES HAVING IMPROVED BIOCOMPATIBILITY AND DEVICE FOR CARRYING OUT THE PROCESS

[75] Inventor: Michael Diamantoglou, Erlenbach, Fed. Rep. of Germany

[73] Assignee: Akzo N.V., Arnhem, Netherlands

[21] Appl. No.: 344,967

[22] Filed: Apr. 28, 1989

[30] Foreign Application Priority Data

Apr. 28, 1988 [DE] Fed. Rep. of Germany ....... 3814326

[51] Int. Cl.$^5$ ............................................. B01D 67/00
[52] U.S. Cl. ................................ 524/35; 210/500.29; 422/129
[58] Field of Search ...................... 210/500.29, 500.24, 210/500.3, 500.31, 500.32; 427/245–246; 534/35–46; 422/129, 131, 134, 135, 138

[56] References Cited

U.S. PATENT DOCUMENTS

| | | |
|---|---|---|
| 472,393 | 4/1892 | Pfeil . |
| 3,865,615 | 2/1975 | Manly . |
| 4,051,040 | 9/1977 | Hazdra et al. . |
| 4,184,811 | 1/1980 | Walch et al. . |
| 4,210,529 | 7/1980 | Petersen . |
| 4,276,172 | 6/1981 | Henne et al. . |
| 4,326,532 | 4/1982 | Hammar . |
| 4,668,396 | 5/1987 | Baurmeister et al. . |
| 4,741,927 | 5/1988 | Pelger et al. . |
| 4,787,977 | 11/1988 | Nakano et al. ................. 210/500.29 |
| 4,834,882 | 5/1989 | Kataoka et al. . |

FOREIGN PATENT DOCUMENTS

| | | |
|---|---|---|
| 0013181 | 7/1980 | European Pat. Off. . |
| 0026618 | 4/1981 | European Pat. Off. . |
| 0095554 | 12/1983 | European Pat. Off. . |
| 1720087 | 6/1971 | Fed. Rep. of Germany . |
| 2300496 | 7/1973 | Fed. Rep. of Germany . |
| 2705735 | 8/1978 | Fed. Rep. of Germany . |
| 2748858 | 5/1979 | Fed. Rep. of Germany . |
| 212649 | 7/1983 | Fed. Rep. of Germany . |
| 3309657 | 9/1983 | Fed. Rep. of Germany . |
| 3341113 | 5/1985 | Fed. Rep. of Germany . |
| 3438531 | 4/1986 | Fed. Rep. of Germany . |
| 3524596 | 1/1987 | Fed. Rep. of Germany . |
| 57-162701 | 10/1982 | Japan . |
| 57-162702 | 10/1982 | Japan . |
| 60-203265 | 10/1985 | Japan . |

OTHER PUBLICATIONS

"Biocompatibility of Hemodialysis Membranes", *Asaio Journal*, Apr./Jun., 1984, vol. 7.
"Anaphylatoxin Formation During Hemodialysis: Effects of Different Dialyzer Membranes" by Dennis E. Chenoweth, Alfred K. Cheung, and Lee W. Henderson, Kidney International, vol. 24, 1983, pp. 764–769.

*Primary Examiner*—Frank Sever
*Attorney, Agent, or Firm*—Oliff & Berridge

[57] ABSTRACT

The invention relates to an apparatus and process for the chemical modification of cellulosic dialysis membranes, wherein solutions of acid chlorides, acid anhydrides, esters, ketenes, diketenes, chlorocarbolic acid esters, carbonic acid diesters, 2,5-diketooxazolidines, isatinic anhydride, isocyanates, carbamoyl chlorides, thiocyanates, thiocarbamoyl chlorides, sulfonyl chlorides, sulfonic acid anhydrides, N-chlorosulfonamides, sulfinic acid chlorides, N-chlorosulfinamides, phosphoric acid anhydride, phosphonic anhydrides, phosphonic acid chlorides, phosphorous acid, phosphinic acid anydrides, ethylene oxide, ethylene sulfide, ethyleneimino, lactone, sultone and/or cleavable onium compounds, alkylaminoethanol sulfate esters, alkylsulfonethanol sulfate esters, vinylsulfonic acid or a salt thereof, vinylsulfonic acid ester, vinylphosphonic acid or a salt thereof, vinylphosphonic acid esters, allylsulfonic acid or a salt thereof, allysulfonic acid esters, allylphosphonic acid or a salt thereof, allyphosphonic acid esters, acrylamide, methacrylamide, acrylic acids or a salt thereof, acrylic acid ester, methacrylic acid or a salt thereof, methacrylic acid esters, acrylonitrile, crotonic acid or a salt thereof and/or crotonic acid ester and/or crotonic acid nitrile in polar solvents, if necessary together with the catalysts and auxiliary substances necessary for the reaction, are passed over one surface of the dialysis membrane.

17 Claims, 4 Drawing Sheets

PROCESS FOR PRODUCING CELLULOSIC DIALYSIS MEMBRANES HAVING IMPROVED BIOCOMPATIBILITY AND DEVICE FOR CARRYING OUT THE PROCESS

BACKGROUND OF THE INVENTION

The invention relates to chemical modification of cellulosic dialysis membranes for improvement of biocompatibility.

U.S. Pat. No. 3,745,202 and German Offenlegungsschrift No. 2,300,496 describe processes for making asymmetric membranes from celluose derivatives containing ester and/or ether groups.

German Pat. No. 2,705,735 discloses a dialysis membrane for hemodialysis, having antithrombogenic compounds chemically bonded thereto, the dialysis membrane consisting of two or more layers of a cellulose regenerated from cuprammonium cellulose solutions, each of which has been obtained from separately fed orifices of a spinneret, which cellulose contains chemically bonded substances having antithrombogenic activity.

German Offenlegungsschrift No. 2,748,858 describes the preparation of antithrombogenic polymer materials which are prepared by the following procedure:

reaction of reactive polymers with synthetic fibrinolytic compounds (covalent bonding), treatment of polymers containing anion-exchange groups with a synthetic fibrinolytic compound (ionic bonding), treatment of polymer materials with solutions of synthetic fibrinolytic compounds (adsorption).

Such a membrane modification is ruled out, because biocompatibility-improving compounds which are bound only adsorptively to the polymer can pass into the bloodstream during dialysis.

U.S. Pat. No. 3,475,410 and the paper in Vol. XII Trans. Amer. Soc. Artif. Int. Organs, 1966, pp. 139–150 describe antithrombogenic cellulose membranes which are obtained by treatment of cellulose first with ethyleneimine and then with heparin. According to our investigations, however, membranes modified with ethylamino groups have poorer biocompatibility than unmodified membranes.

Japanese Applications JP Nos. 57-162,701 and 57-162,702 also claim antithrombogenic cellulose membranes. These are prepared by grafting vinyl monomers onto cellulose or cellulose derivatives, followed by heparinization. In addition to the grafting reaction, however, it is known that a homopolymerization can also occur. Although no permanent bond exists between the homopolymer and the cellulose, the homopolymer cannot be removed completely from the membrane despite intensive washing. Therefore small quantities of the homopolymer can always pass into the bloodstream during blood dialysis.

Japanese Patent Application No. 60-203,265 describes high molecular weight cellulose products for the preparation of medical instruments with anticoagulant properties. Such products are mixtures of polycationic anc polyanionic cellulose derivatives, and are usually obtained by mixing appropriate polymer solutions. Such water-insoluble salts are unsuitable as membrane materials, since the danger is always present that they will be transformed by salt-interchange effects into a compound which is water-soluble or which swells greatly in water.

However, it has also been proposed in German Offenlegungsschrift No. 1,720,087 that by reacting the polymeric material of the membrane with an alkyl halide and then reacting the resulting material with an alkali metal salt of an antithrombogenic compound having a cationic residue (for example, heparin or a heparinoid compound) the risk of blood coagulation is diminished. The possible alkyl halides in this context also include haloalkyldialkylamines. Cellulose and cellulose acetate are among the possible polymers.

An antithrombogenic effect of these known dialysis membranes is observed only when the degree of substitution of the modified cellulose is high, i.e., greater than at least 0.1, and a preheparinization with a relatively high heparin concentration (0.1 to 1% by weight solution) is carried out in a separate stage.

German Offenlegungsschrift No. 3,341,113 discloses a dialysis membrane in the form of flat films, tubular films or hollow filaments of regenerated cellulose, in which polymeric acids are chemically bonded to at least one membrane surface by means of bridge-forming agents which are chemically bonded to the cellulose. Aside from the fact that the preparation is relatively expensive even though it is carried out in a post-treatment, the effectiveness is essentially limited to reduction of leukopenia. Because of the large molecules of the polymeric acids, bonding by means of bridge-forming agents occurs only at the surface of the membrane.

German Offenlegungsschrift No. 3,438,531 discloses a dialysis membrane in which isocyanate prepolymers are bonded to cellulose. The effectiveness is limited in a manner similar to that for the above-mentioned cellulose membrane modified with polymeric acids.

German Offenlegungsschrift No. 3,524,596 discloses a dialysis membrane with improved biocompatibility, which is distinguished in that the mean degree of substitution of a modified cellulose is from 0.02 to 0.07. The known dialysis membrane composed of modified cellulose preferably contains such a modified cellulose which has a structure represented by the formula where X represents —NR″— and/or —N+R″$_2$— and/or —S— and/or —SO— and/or —SO$_2$— and/or —CO—NR— and/or —CO—O— and/or —O—, Y represents —R and/or —NR$_2$ and/or —Si(OR″)$_3$ and/or —SO$_3$H and/or —COOH and/or —PO$_3$H$_2$ and/or —N+HR$_2$ and the salts thereof,

R′ represents an alkylene group and/or cycloalkylene group and/or arylene group having a total of from 1 to 25 C atoms, R″ represents a hydrogen atom or R, and R represents an alkyl group having 1 to 5 C atoms and/or a cycloalkyl group and/or aryl group.

This known dialysis membrane is capable of reducing to a considerable extent blood coagulation, leukopenia and complement activation. However, no noteworthy extent of adsorption of beta-2-microglobulin has been achieved.

German Patent Application No. P 3,723,897.3 describes cellulose derivatives having the general formula in which —Z— denotes an alkylene, alkenylene, alkynylene, cycloalkylene or benzylene or xylylene radical which may or may not be substituted, X denotes —H, —$NR_2$, —$N^+R_3$, —CN, —COOH, —$SO_3H$, —$PO(OR)_2$, —$CONR_2$ or —$Si(OR)_3$, where R denotes a hydrogen atom or an alkyl or alkenyl group having from 1 to 25 C atoms, or a cycloalkyl, tolyl or phenyl group, and Y is an alkyl, alkenyl or alkynyl group, which may or may not be substituted, having from 1 to 36 C atoms, a cycloalkyl group or a phenyl, tolyl or benzyl group or a or (—CH=CH—COOH) or NH—R radical and R has the same meaning as above, and r=1–20,
m=0–2.5,
n=0.2 to 2.95, with the proviso that, where m=0, n>1.55 when Y is an alkyl radical having 1–5 C atoms, a —$(CH_2)_r$—COOH radical with r=0, 1 or 2 or a radical of phthalic acid, and the degree of polymerization is more than 400, and which can be prepared by homogeneous reaction in a mixture of dimethyl acetamide and/or N-methylpyrrolidone with LiCl after activation of the cellulose starting material without the presence of LiCl, the preparation thereof and the use thereof for membranes and filaments.

German Patent Application No. P 3,805,992.4 relates to modified cellulose for biocompatible dialysis membranes, which cellulose has a structure represented by the formula wherein Cell is cellulose or chitin, in each case without hydroxyl groups, s=3 in the case of cellulose and s=2 in the case of chitin, and R' is $CH_3$ and/or $C_2H_5$ and/or $C_3H_7$,
X is a specified functional group, and
wherein
R" is H or R,
x+t=1.00 to 2.50,
x=0 to 0.5 t,
r=0.01 to 0.45, and the degree of polymerization (DP) is 100 to 500, as well as a process for preparation of the cellulose derivatives.

German Patent Application No. P 3,805,966.5 relates to modified cellulose for biocompatible dialysis membranes, which cellulose has a structure represented by the formula wherein Cell is unmodified cellulose or chitin, in each case without hydroxyl groups, s=3 in the case of cellulose and s=2 in the case of chitin, and wherein
R' is $CH_3$ and/or $C_2H_5$ and/or $C_3H_7$,
X is a specified functional group, and
m=1.00 to 2.50,
x=0.01 to 0.45, and the degree of polymerization (DP) is 100 to 500, as well as a process for preparation of the modified cellulose derivatives.

German Patent Application No. P 3,805,973.8 relates to modified cellulose for biocompatible dialysis membranes, wherein the modified cellulose has a structure represented by the formula wherein Cell is cellulose or chitin, in each case without hydroxyl groups, s=3 in the case of cellulose and s=2 in the case of chitin, and wherein
R' is $CH_3$ and/or $C_2H_5$ and/or $C_3H_7$,
X is a specified functional group, and
Z corresponds to the following groups of atoms: SR", $SO_3H$ or a salt thereof, SO—R, $SONR"_2$, $SO_2$—R, $SO_2NR"_2$, $SO_2H$ or a salt thereof, F, Cl, Br, I, $NR"_2$, $PR"_2$, $PO_3H_2$ or a salt thereof, $PO_2H(OR)$, $PO(OR)_2$, $PO_2HR"$ or a salt thereof, POR"(OR), $POR"_2$, wherein
R" is H or R,
x+t=1.0 to 2.50,
x=0 to 0.5 t,
z=0.01 to 0.45, and the degree of polymerization (DP) is 100 to 500, as well as a process for preparation of the cellulose derivatives.

Apart from the circumstance that dialysis membranes composed of synthetic or natural polymers can, when used in artificial kidneys, very easily induce blood coagulation, which is substantially prevented by appropriate drug treatment, in the case of dialysis membranes composed of regenerated cellulose there is frequently a transient fall in leukocytes in the first period of dialysis treatment when a kidney patient is treated with dialyzers having cellulose membranes. This effect is called leukopenia. Leukopenia is a reduction in the number of leukocytes (white blood corpuscles) in the circulating blood. The number of white blood corpuscles in humans is about 4,000 to 12,000 cells/$mm^3$.

Leukopenia associated with dialysis is most pronounced 15 to 20 min after the start, it being possible for the neutrophils (which are the leukocytes which can be stained with neutral or simultaneously with acidic and basic dyes) to disappear almost completely. Subsequently, the number of leukocytes recovers again within about one hour to almost the initial level or exceeds it.

If, after the leukocytes have recovered, a new dialyzer is connected, leukopenia occurs again to the same extent.

Cellulose membranes cause pronounced leukopenia. Even though the clinical significance of leukopenia has not been scientifically elucidated, there is nevertheless a desire for a dialysis membrane for hemodialysis which does not exhibit the leukopenia effect, without this adversely affecting the other very desirable properties of dialysis membranes composed of regenerated cellulose.

During hemodialysis using membranes composed of regenerated cellulose, beside the leukopenia there has also been found a distinct complement activation. The complement system within the blood serum is a complex plasma-enzyme system which consists of many components and acts in various ways to prevent damage due to invading foreign cells (bacteria etc.). When antibodies against the invading organism are present, there can be complement-specific activation by the complex of the antibodies with antigenic structures of the foreign cells, otherwise complement activation takes place by an alternative pathway due to special surface features of the foreign cells. The complement system is based on a multiplicity of plasma proteins. After activation, these proteins react specifically in a defined sequence with one another and, finally, a cell-damaging complex which destroys the foreign cell is formed.

Individual components release peptides which induce inflammatory manifestations and occasionally can also have undesired pathological consequence for the organism. It is assumed that in the case of hemodialysis membranes composed of regenerated cellulose the activation takes place by the alternative pathway. These complement activations are detected objectively by determination of the complement fragments C3a and C5a.

In this context, reference is made to the following studies: D. E. Chenoweth et al., Kidney International, vol. 24, pages 746 et seq., 1983 and D. E. Chenoweth, Asaio-Journal, vol. 7, pages 44 et seq., 1984.

The carpal tunnel syndrome is affected by modified cellulose derivatives. Yet, there is a considerable need for further modifications of the cellulose in order to eliminate this phenomenon too as completely as possible.

BRIEF SUMMARY OF THE INVENTION

An object of the invention is to improve the biocompatibility of cellulosic, i.e., of modified and unmodified cellulose membranes as well as membranes having a chitin base by post-treatment. In the process, there must be no or only minor impairment of the dialysis and mechanical properties. The linking of the modifying agent with the polymer is to be effected only by means of a covalent bond having sufficient hydrolysis and storage stability which even survives membrane sterilization. During blood dialysis, no modifying agent must pass into the bloodstream.

In one aspect, the present invention relates to a process for the chemical modification of cellulosic dialysis membranes in the form of flat films, tubular films or tubular filaments, comprising contacting at least one surface of a cellulosic membrane with a solution of a polar solvent having dissolved therein at least one member selected from the group consisting of acid chlorides, acid anhydrides, acids, esters, ketenes, diketenes, chloroformic acid esters, carbonic acid diesters, 2,5-diketooxazolidines, isatinic anhydride, isocyanates, carbamoyl chlorides, thiocyanates, thiocarbamoyl chlorides, sulfonyl chlorides, sulfonic acid anhydrides, N-chlorosulfonamides, sulfinic acid chlorides, N-chlorosulfinamides, phosphoric acid anhydride, phosphonic acid anhydrides, phosphonic acid chlorides, phosphorous acid, phosphinic acid anhydrides, ethylene oxide, ethylene sulfide, ethyleneimino, lactone, sultone, cleavable onium compounds, alkylaminoethanol sulfate esters, alkylsulfonethanol sulfate esters, vinylsulfonic acid, a salt of vinylsulfonic acid, vinylsulfonic acid esters, vinylphosphoric acid, a salt of vinylphosphoric acid, vinylphosphoric acid esters, allylsulfonic acid, a salt of allylsulfonic acid, allylsulfonic acid esters, allylphosphonic acid, a salt of allylphosphonic acid, allylphosphonic acid esters, acrylamide, methacrylamide, acrylic acid, a salt of acrylic acid, acrylic acid esters, methacrylic acid, a salt of methacrylic acid, methacrylic acid esters, acrylonitrile, crotonic acid, a salt of crotonic acid, crotonic acid esters, and crotonic acid nitrile.

Another aspect of the invention relates to an apparatus for carrying out the process of claim 1, comprising a piping system which is in communication with at least one storage tank for liquid or gas and with at least one membrane module, and a conveying means to maintain a liquid circulation, wherein the piping system is a ring circuit to which the storage tank is attached through a proportioning device adapted to supply said liquid or gas at a predesignated time and in predesignated quantity from said storage tank through the ring circuit to said membrane module.

DETAILED DESCRIPTION OF THE PREFERRED EMBODIMENTS

As summarized above, the objects of this invention are achieved by a process which is characterized in that solutions of acid chlorides and/or acid anhyrides and/or acids and/or esters and/or ketenes and/or diketenes and/or chloroformic acid esters and/or carbonic acid diesters and/or 2,5-diketooxazolidines and/or isatinic anhydride and/or isocyanates and/or carbamoyl chlorides and/or thiocyanates and/or thiocarbamoyl chlorides and/or sulfonyl chlorides and/or sulfonic acid anhydrides and/or N-chlorosulfonamides and/or sulfinic acid chlorides and/or N-chlorosulfinamides and/or phosphoric acid anhydride and/or phosphonic acid anhydrides and/or phosphonic acid chlorides and/or phosphorous acid and/or phosphinic acid anhydrides and/or ethylene oxide and/or ethylene sulfide and/or ethyleneimino and/or lactone and/or sultone and/or cleavable onium compounds and/or alkylaminoethanol sulfate esters and/or alkylsulfonethanol sulfate esters and/or vinylsulfonic acid or a salt thereof and/or vinylsulfonic acid esters and/or vinylphosphoric acid or a salt thereof and/or vinylphosphoric acid esters and/or allylsulfonic acid or a salt thereof and/or allylsulfonic acid esters and/or allylphosphonic acid or a salt thereof and/or allylphosphonic acid esters and/or acrylamide and/or methacrylamide and/or acrylic acid or a salt thereof and/or acrylic acid esters and/or methacrylic acid or a salt thereof and/or methacrylic acid esters and/or acrylonitrile and/or crotonic acid or a salt thereof and/or crotonic acid esters and/or crotonic acid nitrile in polar solvents, if necessary together with catalysts and auxiliary substances necessary for the reaction, are passed over one surface of the dialysis membrane.

The post-treatment of cellulose structures is not new as such. Especially in the years around 1960, it was the subject matter of numerous studies and publications with the objective of imparting specified properties such as crease recovery, hydrophobicity, flame retardancy or dirt resistance to cellulosic fabrics. The finishing process is normally performed by impregnating the cellulose fabric with the aqueous solution of the modifying agent, squeezing to the desired moisture absorption, predrying at 100° C. and fixing at 120° to 150° C. Thereafter the fabrics are thoroughly washed and dried. In some cases, organic solvents are also used as finishing media. However, in attempts to modify dialysis membranes by these procedures, it is found that the membranes largely lose their dialysis properties.

The "post-modification of membranes for the purpose of improving biocompatibility while preserving the other membrane properties" is, as an example, carried out according to the invention in the following general manner:

The modifying agent and if necessary the auxiliary agents necessary for the reaction (catalyst, acid-bonding agent) are dissolved in an organic polar solvent, the modifying agent and auxiliary agent being able to be dissolved together, or separately for reasons of compatibility and solubility, and even in different polar solvents. Depending on the modifying agent, the membrane modification is carried out either at room temperature or at higher temperatures. After modification, the membranes are thoroughly washed with washing agents in which both the modifying agents and secondary products which may result during the reaction are soluble. In the case that the washing agent has a high boiling point or is water, it is replaced by a low-boiling organic solvent such as alcohol, acetone, etc., which if necessary can also contain a softening agent. The membranes are then dried with air or nitrogen at 20° to 70° C. By means of this procedure, biocompatible dialysis membranes are obtained which are modified not only at the surface but completely through the interior and which largely have the same dialysis properties as before modification.

Suitable polar solvents can be alcohols containing 1 to 8 C atoms and/or ethers and/or esters and/or ketones and/or amide solvents and/or sulfide solvents and/or nitro-group-containing solvents and/or nitrile-group-containing solvents and/or halohydrocarbons and/or tertiary amines and/or amides.

Examples of "polar" solvents include hydroxy compounds, ethers, esters and ketones, for example alcohols containing 1 to 8 C atoms, glycols such as neopentyl glycol, diethylene glycol, triethylene glycol, polyethylene glycols, cyclohexanols such as cyclohexanol, methylcyclohexanol, benzyl alcohol, furfuryl alcohol, ethyl glycol, propyl glycol, butyl glycol, hexyl diglycol, diglycol dimethyl ether, propylene glycol dimethyl ether, tripropylene glycol methyl ether, triethylene glycol dimethyl ether, hexyl glycol, methyl diglycol, ethyl diglycol, butyl diglycol, methyl triglycol, ethyl triglycol, butyl triglycol, ethylene glycol dimethyl ether, triethylene glycol dimethyl ether, diethylene glycol diethyl ether, methyl propyl ketone, methyl isopropyl ketone, methyl butyl ketone, methyl isobutyl ketone, methyl amyl ketone, methyl isoamyl ketone, methyl heptyl ketone, diethyl ketone, ethyl butyl ketone, ethyl amyl ketone, diisopropyl ketone, diisobutyl ketone, methylcyclohexanone, 3-methylcycloheptan-5-one, mesityl oxide, acetylacetone, isopropyl acetate, butyl acetate, isobutyl acetate, sec-butyl acetate, amyl acetate, isoamyl acetate, hexyl acetate, cyclohexyl acetate, benzyl acetate, methyl propionate, ethyl propionate, propyl propionate, n-butyl propionate, ethyl butyrate, propyl butyrate, n-butyl butyrate, isobutyl butyrate, amyl butyrate, methyl isobutyrate, ethyl isobutyrate, isopropyl isobutyrate, isobutyl isobutyrate, ethyl acetate, butyl acetate, glycolic acid butyl ester, methyl glycol acetate, ethyl glycol acetate, butyl glycol acetate, ethyl diglycol acetate, butyl diglycol acetate, 3-methoxybutyl acetate, ethylene carbonate and propylene carbonate. However, the preferred substances from this solvent group are water, alcohols containing 1 to 4 carbon atoms, ethylene glycol, diethylene glycol, propanediol, butanediol, glycerol, dioxane, methyl glycol, ethyl glycol, acetone, methyl ethyl ketone, cyclohexanone, methyl acetate, ethyl acetate, propyl acetate, ethylene carbonate, propylene carbonate, if necessary in a mixture with other polar solvents.

Examples of other suitable solvents are amides and amines such as pyridine, N-methylmorpholine, N-methylpiperidine and dimethylpropyleneurea. The preferred solvents are dimethylformamide, dimethylacetamide, N-methylpyrrolidone, dimethylethyleneurea and trialkylamines, if necessary in a mixture with other polar solvents.

Examples of other suitable solvents are nitro compounds such as nitroethane, nitropropane and nitrobenzene. A preferred solvent is nitromethane, if necessary in a mixture with other polar solvents.

Examples of other suitable solvents are nitrides such as propionitrile or butyronitrile. A preferred solvent is acetonitrile, if necessary in a mixture with other polar solvents.

Examples of other suitable solvents are sulfur and phosphorus compounds such as dimethyl sulfone, sulfolane and hexamethylphosphoric triamide. A preferred solvent is dimethyl sulfoxide, if necessary in a mixture with other polar solvents.

Examples of other suitable solvents are chlorinated hydrocarbons such as 1,1-dichloroethane, 2-chlorobutane, 1,1,1-trichloroethane, carbon tetrachloride, 1-chlorobutane, 1,2-dichloroethane, trichloroethylene, perchloroethylene, 1,1,2,2-tetrachloroethane, dichlorodiethyl ether, o-dichlorobenzene and o-chlorotoluene.

The preferred solvents are chloropropane, methylene chloride, chloroform or chlorobenzene, if necessary in a mixture with other polar solvents.

Figure 1:
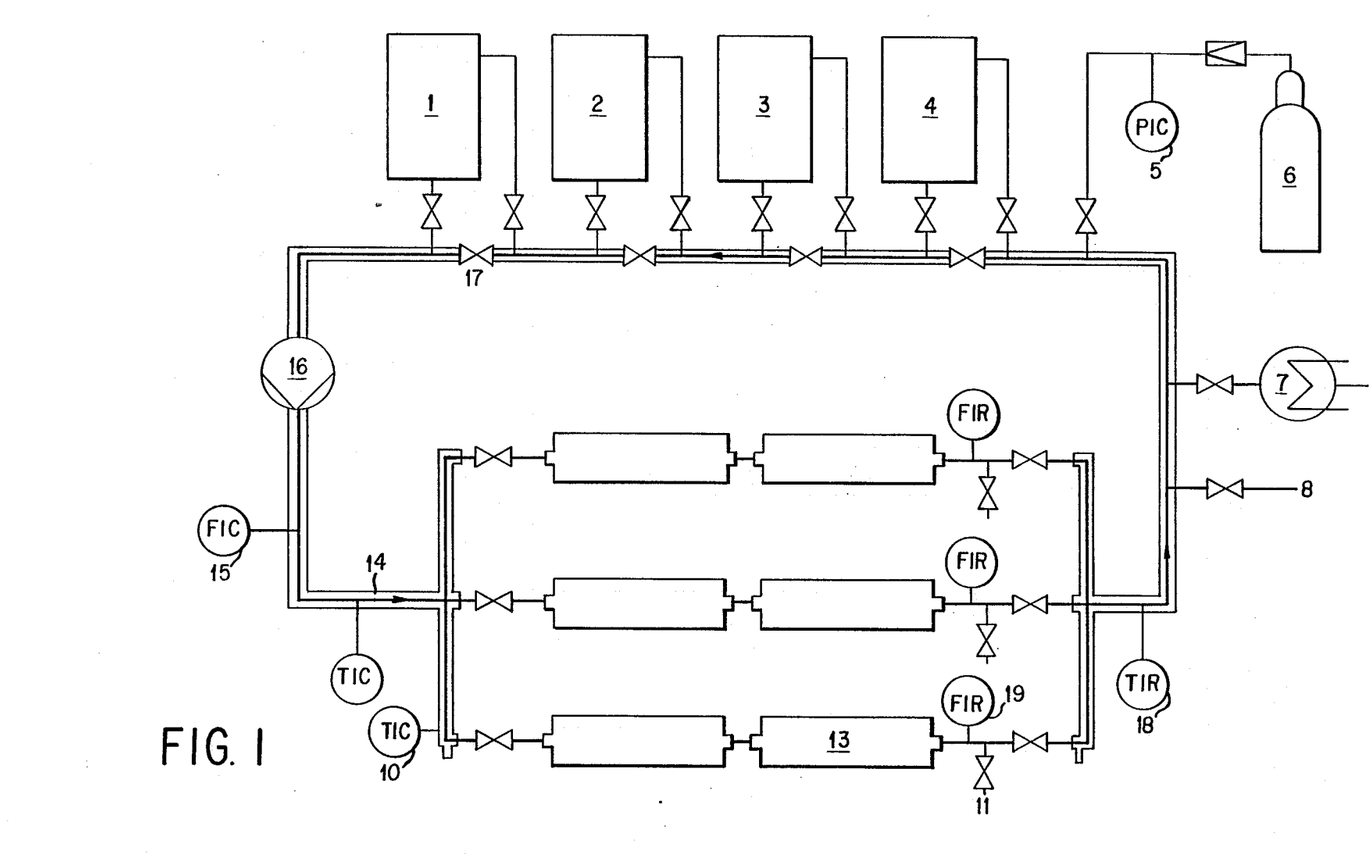
FIG. 1 illustrates an apparatus suitable for practicing the claimed method.

The subject matter of the invention includes an apparatus for carrying out the process. As illustrated in FIG. 1, it comprises a piping system (14), which is in communication with one or more supply tanks for liquids (1, 2, 3, 4) and/or gases (6) and with one or more membrane modules (13) and a conveying device (16) to maintain a liquid circulation, the piping system (14) being a closed circular pipe, to which the storage tanks (1, 2, 3, 4, 6) are attached in series through proportioning devices (17). The proportioning devices (17) are designed in such a way that the reagents, solvents and/or washing agents can be supplied at predesignated times and in predesignated quantities through the closed circular pipe to at least one compartment of the membrane modulue (13).

By membrane modules, units containing membranes in the form of flat films, tubular films or hollow filaments are to be understood in the broadest sense within the scope of the invention. They can be permanently mounted in a casing equipped with connecting pieces or can be assembled in any other manner with or without sealing means, for example in the form of a hollow-filament bundle provided with a tubular sheath.

Figure 2:
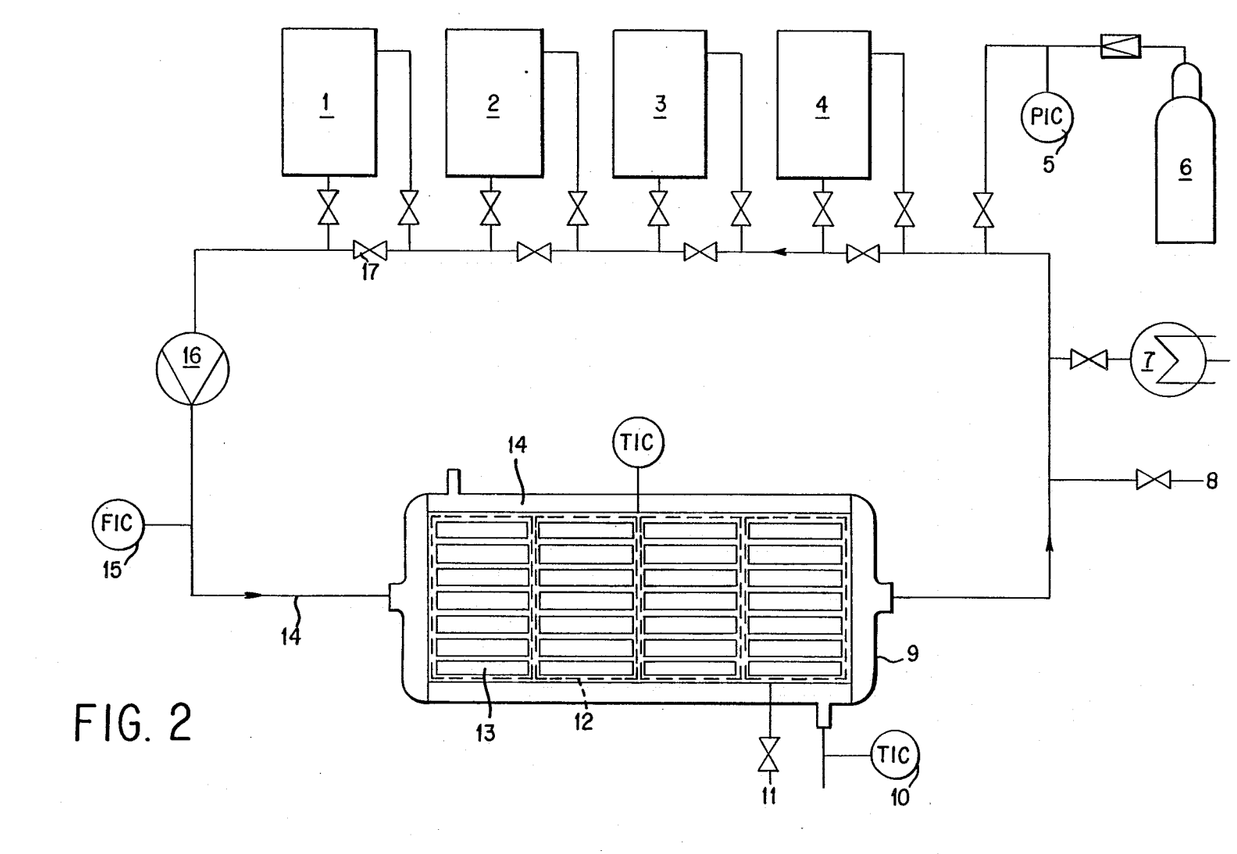
FIG. 2 illustrates another embodiment of the claimed apparatus.

Preferably a plurality of membrane modules is placed in one holding container (12) provided with flow holes and one or more holding containers (12) is or are placed in a reaction vessel (9), which is interposed in the closed circular pipe (14), as is illustrated in FIG. 2. In this connection the membrane modules are disposed in as close-packed manner as possible in holding container (12).

For subsequent modification of membrane modules, including hollow-filament bundles and flat membranes, the apparatuses schematically illustrated in FIGS. 1 and 2 are very suitable.

In FIG. 1, a plurality of membrane modules (13) is directly in communication with the closed circular pipe of piping system (14). Of the individual reference numerals therein, (1) is a storage tank for reagent solution, for example, (2) a storage tank for auxiliary-agent solution (catalyst, acid-bonding agent), for example, (3) a storage tank for solvent, for example, (4) a storage tank for softener-containing washing solution, for example, (5) a pressure gauge and controller, (6) a storage tank for gases, (7) a condenser, (8) an air vent, (10) a temperature gauge and controller, (11) a drain, (13) a membrane module, (14) the piping system, (15) a flowmeter and flow controller, (16) a conveying device, (17) a proportioning device, (18) a temperature gauge and recorder, (19) a flowmeter and flow recorder.

FIG. 2 shows the preferred embodiment according to claim 13, wherein (12) denotes the holding container and (9) denotes the reaction vessel. The other reference numerals have the same meaning as in FIG. 1.

Figure 3:
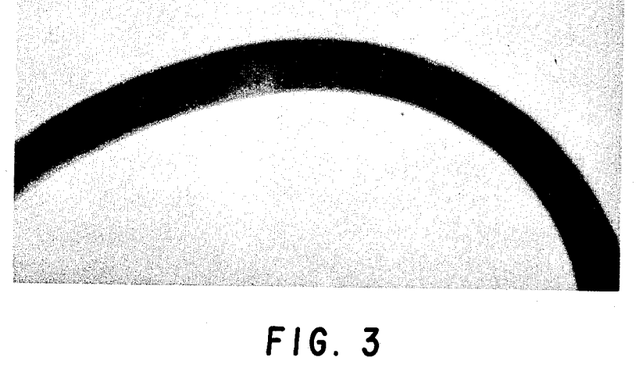
FIG. 3 is a photograph of a section of the cellulosic membrane discussed in Example 20 which has been post-treated according to the claimed method and then stained with a basic dye.
Figure 4:
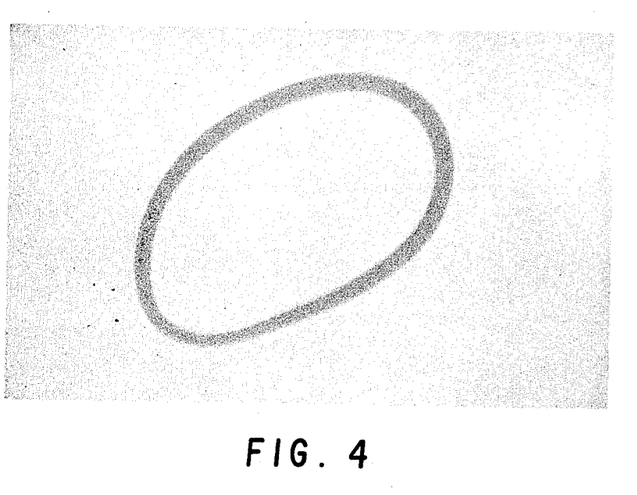
FIG. 4 is a photograph of another section of the cellulosic membrane of Example 20 which has been post-treated according to the claimed method and subsequently stained with a basic dye.

FIGS. 3 and 4 are photographs of sections of membranes according to the invention, which membranes have been stained with a basic dye that does not stain the unmodified cellulose. It is clearly evident that the staining is homogeneous in the entire cross section, which confirms that the modification occurs over the entire filament cross section, even though the reagents were in contact only with the surface of the cellulose.

Figure 5:
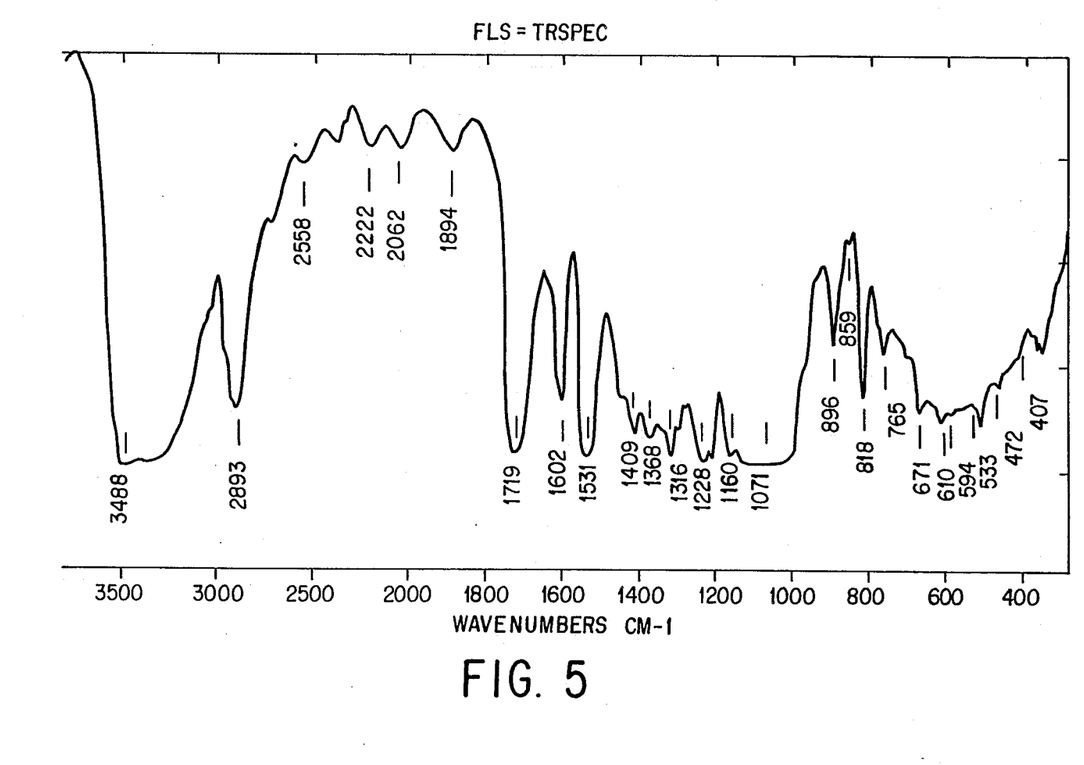
FIG. 5 shows the IR spectrum of the cellulose membrane discussed in Example 24, modified according to the invention.

FIG. 5 shows the IR spectrum of the cellulose membrane according to Example 24, modified according to the invention.

The complement activation within the scope of the present invention was assessed on the basis of the C5a fragments. For this purpose, 300 ml of heparinized blood plasma was recirculated in vitro through a dialyzer with an effective exchange area of 1 m$^2$ at a plasma flow rate of 100 ml/min for a period of 4 hours. The C5a fragments in the plasma were determined using the RIA method (Upjohn assay). The relative complement activation for the particular time of measurement was calculated as a percentage by forming the ratio of the concentration at the time of sampling with the initial value. The measurement after a recirculation time of 4 hours was used for the evaluation. Flat membranes were incubated with heparinized blood plasma for 3 hours and then the C5a fragments were determined.

The increase in the beta-2-microglobulin level in long-term dialysis patients is observed after use of membranes composed of regenerated cellulose and is attributed to these membranes being less permeable to substances in the molecular weight range 1,000 to 20,000 and the microglobulins thus being removed to an insufficient extent during the dialysis. Beta-2-microglobulin is not adsorbed to a noteworthy extent onto customary membranes composed of regenerated cellulose. However, the cellulose derivatives according to the invention can contribute in an unexpected manner to this.

The beta-2-microglobulin content adsorbed onto the membrane is measured within the scope of the invention in the following manner.

10 ml of human blood plasma are added to each 500 mg of substance (dialysis membrane) and incubated at 37° C. for 30 minutes. The human blood plasma contains 13.67 mg/liter of beta-2-microglobulin. The sample is centrifuged at 3,000 r.p.m. for 15 minutes. The beta-2-microglobulin content in the supernatant is determined. The sample is then washed 2 times with 10 ml of phosphate-buffered saline each time. The microglobulin content in the washings is also determined. The percentage amount of beta-2-microglubulin adsorbed can be calculated from the difference between the original and the unabsorbed beta-2-microglobulin.

The average degree of polymerization DP was determined in a cupriethylenediamine solution by the DIN 54270 method.

The degree of etherification and/or degree of esterification were determined on the basis of the analytical results which are known and typical for the substituents, for example nitrogen by the Kjeldahl method, sulfur by the Schoniger method or phosphorus by the molybdate method, where appropriate from the difference between before and after saponification.

For esterification, the known catalysts such as bases, acids, basic salts, etc. can be applied. Because of the danger of decomposition of the cellulose, however, bases and basic salts are preferably used.

Known catalysts can also be used in the reaction with isocyanates. For reasons of decomposition, tertiary bases are preferably used.

Known agents are also used in the etherification reaction.

The invention will be further illustrated by means of the examples presented hereinafter.

EXAMPLE 1

486 g (3 mol) of cellulose hollow filaments were placed in a reactor corresponding to that of FIG. 2. The apparatus was filled completely with a solution consisting of 3 liters of dimethylacetamide, 60 g (0.45 mol) of p-tolyl isocyanate and 5 ml of triethylamine, the air being completely removed from the hollow filaments and the installation by suction. The reactor was heated to 50° C. and the solution circulated for 24 hours by means of a pump. Thereafter the solution containing the modifying agent was drained from the reactor, and the hollow filaments were rinsed with dimethylacetamide, ethanol and finally 1% alcoholic glycerol solution and dried with nitrogen in the reactor at 50° C. The cellulose hollow filaments treated in this way have a nitrogen content of 0.8%, corresponding to a degree of substitution of m=0.10.

The ultrafiltration rate is unchanged, the value being 4 ml/hr.m$^2$.mm Hg at 37° C.

Compared with unmodified hollow filaments, the modified hollow filaments exhibit a lower complement activation. The reduction in C5a compared with the unmodified membrane is 100%.

EXAMPLES 2–8

On the basis of the procedure of Example 1, Cuprophane and chitin hollow filaments were post-treated with a number of isocyanates in dimethylacetamide and catalysts known from the literature, and their complement activation was determined on the basis of the C5a fragments. The results are presented in Table 1.

EXAMPLE 9

16.2 g (0.1 mol) of Cuprophane flat membranes were placed in a cylindrical vessel. A solution consisting of 800 ml of dimethylacetamide, 26.6 g (0.1 mol) of dodecenyl succinate and 2.5 g (0.025 mol) of potassium acetate was then added and the reaction mixture was maintained for 10 hours at 60° C. and for 15 hours at 20° C. Thereafter the membranes were washed with dimethylacetamide, ethanol, water, ethanol and 1% alcoholic glycerol solution and dried in air. The membranes have a dodecenyl group content of m=0.13. The ultrafiltration rate remains unchanged, the value being 2.4 ml/hr.m$^2$.mm Hg at 37° C.

The reduction in C5a compared with the unmodified membrane is 100%. Moreover, the membrane exhibits a beta-2-microglobulin adsorption of 38%.

EXAMPLES 10–18

On the basis of the procedure of Example 9, Cuprophane and chitin flat membranes were post-modified by esterification and were then examined. The results are presented in Table 2.

EXAMPLE 19

486 g (3 mol) of cellulose hollow filaments were placed in a reactor corresponding to that of FIG. 2. The apparatus was filled completely with a solution consisting of 151.5 g (1 mol) of 2,3-epoxypropyltrimethylammonium chloride, 18 g (0.45 mol) of sodium hydroxide and 2850 g of water, the air being completely removed from the hollow filaments and the installation by suction. The reaction solution was circulated for 24 hours at 25° C. by means of a pump and was then drained. The membranes were rinsed with water, ethanol and 1% alcoholic glycerol solution and dried with nitrogen in the reactor at 50° C. The membranes have a nitrogen content of 0.17%, corresponding to a degree of substitution of m=0.02.

The reduction in C5a compared with the unmodified hollow filaments is 78%.

EXAMPLE 20

On the basis of the procedure of Example 19, cellulose hollow filaments were post-modified with vinylsulfonic acid sodium salt and sodium hydroxide as catalyst. The membranes have a degree of modification of m=0.05.

By staining with a basic dye, for example from the Astrazon Blue series, which responds only to acid groups and does not stain unmodified cellulose, it is clearly seen that the modified hollow filaments are homogeneously stained completely through the interior (FIGS. 3 and 4). This indirectly indicates modification completely through the interior.

The reduction in C5a compared with the unmodified membrane is 70%.

EXAMPLE 21

486 g (3 mol) of cellulose hollow filaments were placed in a reactor corresponding to that of FIG. 2. The membranes were made alkaline with 3% aqueous sodium hydroxide solution for 30 minutes at 15° C. and then rinsed with acetone. The apparatus was filled completely with a solution consisting of 81.3 g (0.6 mol) of chloroethyldiethylamine and 2950 ml of i-propanol, the air being completely removed from the hollow filaments and the installation by suction. The reactor was heated to 60° C. and the solution was circulated for 2 hours by means of a pump. After draining of the reaction solution, the membranes were rinsed with water, ethanol and 1% alcoholic glycerol solution and dried with nitrogen in the reactor at 50° C. The membranes have a nitrogen content of 0.21%, corresponding to a degree of substitution of m=0.025.

The reduction in C5a compared with the unmodified membrane is 85%.

EXAMPLE 22

On the basis of the procedure of Example 21, cellulose hollow filaments were post-modified with acrylonitrile in 1,2-dichloroethane and sodium hydroxide as catalyst. The membranes have a degree of modification of m=0.08.

The reduction in C5a compared with the unmodified membrane is 94%.

EXAMPLE 23

On the basis of the procedure of Example 21, cellulose hollow filaments were post-treated with ethyleneiminosuccinic acid diethyl ester in dimethylacetamide and methanesulfonic acid as catalyst. Membranes having a degree of substitution of m=0.023 are obtained.

The reduction in C5a compared with the unmodified membrane is 68%.

EXAMPLE 24

32.4 g (0.2 mol) of cellulose hollow filaments were processed to form a module and were connected to an apparatus corresponding to FIG. 1. The apparatus was filled completely with a solution consisting of 8 g (0.06 mol) of p-tolyl isocyanate, 1 ml of triethylamine and 500 ml of dimethylacetamide, the air being completely removed by suction. The membranes were treated with the reaction solution, first for 7 hours at 50° C. and then for 15 hours at 25° C. In the process, the solution was circulated continuously by means of a pump. After the solution had been removed, the membranes were rinsed with dimethylacetamide, ethanol and 1% alcoholic glycerol solution and dried with nitrogen at 50° C. The resulting membranes contain 0.45% nitrogen, corresponding to a degree of substitution of m=0.06.

The IR spectrum (FIG. 5) shows the bands characteristics of an aromatic urethane at 1719, 1531 and 1602 cm$^{-1}$.

The reduction in C5a compared with the unmodified membrane is 98%.

EXAMPLES 25–28

On the basis of the procedure of Example 1 or 9, chitosan membranes were post-modified with isocyanates or by esterification and were then examined. The results are presented in Table 3.

TABLE 1

General formula: $\text{Cell}\diagdown^{[OH]_{n-m}}_{[OX]_m}$ (Cell = cellulose or chitin molecule without OH groups)

| Example No. | Polymer | n | X | m | C5a reduction, % | Beta-2-microglob. adsorption % |
|---|---|---|---|---|---|---|
| 2 | Cellulose | 3 | C$_4$H$_9$NHCO | 0.15 | 94 | — |
| 3 | Cellulose | 3 | C$_6$H$_{11}$—NHCO | 0.11 | 99 | 10 |
| 4 | Cellulose | 3 | C$_6$H$_5$—NHCO | 0.13 | 100 | — |
| 5 | Cellulose | 3 | C$_{18}$H$_{37}$—NHCO | 0.05 | 93 | 12 |
| 6 | Cellulose | 3 | OCNH—C$_6$H$_4$—NHCO | 0.06 | 82 | — |
| 7 | Cellulose | 3 | OCHN—C$_6$H$_{10}$—NHCO | 0.07 | 86 | 8 |
| 8 | Chitin | 2 | CH$_3$—C$_6$H$_4$—NHCO | 0.12 | 97 | — |

TABLE 2

General formula: $\text{Cell}\diagdown^{[OH]_{n-m}}_{[OX]_m}$ (Cell = cellulose or chitin molecule without OH groups)

| Example No. | Polymer | n | X | m | C5a reduction, % | Beta-2-microglob. adsorption % |
|---|---|---|---|---|---|---|
| 10 | Cellulose | 3 | C$_2$H$_5$CO | 0.55 | 99 | — |
| 11 | Cellulose | 3 | C$_3$H$_7$CO | 0.28 | 96 | — |
| 12 | Cellulose | 3 | C$_{17}$H$_{35}$CO | 0.05 | 93 | — |
| 13 | Cellulose | 3 | C$_{15}$H$_{31}$CH=C(CH$_2$COOH)CO | 0.09 | 100 | 33 |
| 14 | Cellulose | 3 | C$_{11}$H$_{23}$COCH(C$_{10}$H$_{21}$)CO | 0.08 | 95 | — |
| 15 | Cellulose | 3 | C$_{17}$H$_{35}$COCH(C$_{16}$H$_{33}$)CO | 0.05 | 100 | — |
| 16 | Cellulose | 3 | HOOCCH(SO$_3$H)CH$_2$CO | 0.07 | 96 | 43 |
| 17 | Cellulose | 3 | C$_2$H$_5$CO/HOOCH=CHCO | 0.35/ 0.08 | 97 | — |
| 18 | Chitin | 3 | C$_{11}$H$_{23}$CH=C(CH$_2$COOH)CO | 0.06 | 85 | 25 |

TABLE 3

General formula: $\text{Cell}\diagdown^{[OH]_{2-a}}_{\diagdown^{[NH_2]_{1-b}}_{[NHX]_b}}_{[OX]_a}$ (Cell = cellulose without OH groups, and m = a + b)

| Example No. | Polymer | X | m | C5a reduction, % | Beta-2-microglob. adsorption, % |
|---|---|---|---|---|---|
| 25 | Chitosan | CH$_3$—C$_4$H$_6$—NHCO | 0.18 | 90 | — |
| 26 | Chitosan | C$_{18}$H$_{37}$—NHCO | 0.07 | 85 | — |
| 27 | Chitosan | C$_{11}$H$_{23}$CH=C(CH$_2$COOH)CO | 0.10 | 93 | 24 |
| 28 | Chitosan | C$_{15}$H$_{31}$CH=C(CH$_2$COOH)CO | 0.09 | 95 | 28 |

I claim:

1. A process comprising: chemically modifying of cellulosic dialysis membranes in the form of flat films, tubular films or tubular filaments, by, providing properties sufficient for providing properties sufficient for providing a C5A reduction of up to 100%, by
    contacting at least one surface of a cellulosic membrane with a solution of a polar solvent having dissolved therein a preselected concentration of at least one monomer selected from the group consisting of acid chlorides, acid andydrides, acids, esters, ketenes, diketenes, chloroformic acid esters, carbonic acid diesters, 2,5-diketooxazolidines, isatinic anhydride, isocyanates, carbamoyl chlorides, thiocyanates, thiocarbamoyl chlorides, sulfonyl chlorides, sulfonic acid anhydrides, N-chlorosulfonamides, sulfinic acid chlorides, N-chlorosulfinamides, phosphoric acid anhydride, phosphonic acid anhydrides, phosphonic acid chlorides, phosphorous acid, phosphinic acid anhydrides, ethylene oxide, ethylene sulfide, ethyleneimino, lactone, sultone, cleavable onium compounds, alkylaminoethanol sulfate esters, alkylsulfonethanol sulfate esters, vinylsulfonic acid, a salt of vinylsulfonic acid, vinylsulfonic acid esters, vinylphosphonic acid, or a salt of vinylphosphonic acid, vinylphosphonic acid esters, allylsulfonic acid, a salt of allylsulfonic acid, allylsulfonic acid esters, allylphosphonic acid, a salt of allylphosphonic acid, allylphosphonic acid esters, acrylamide, methacrylamide, acrylic acid, a salt of acrylic acid, acrylic acid esters, methacrylic acid, a salt of methacrylic acid, methacrylic acid esters, acrylonitrile, crotonic acid, a salt of crotonic acid, crotonic acid esters, crotonic acid nitrile, and mixtures thereof.

2. The process of claim 1, wherein the polar solvent is selected from the group consisting of alcohols containing 1 to 8 carbon atoms, ethers, esters, ketones, sulfide solvents, nitro-group-containing solvents, nitrile-group-containing solvents, halohydrocarbons, tertiary amines, amides, and mixtures thereof.

3. The process of claim 1, wherein the polar solvent is water.

4. The process of claim 1, wherein the polar solvent is an oxygen-containing solvent selected from the group consisting of ethers, esters, ketones, alcohols containing 1 to 4 carbon atoms, ethylene glycol, diethylene glycol, propanediol, butanediol, glycerol, dioxane, methyl glycol, ethyl glycol, acetone, methyl ethyl ketone, cyclohexanone, methyl acetate, ethyl acetate, propylacetate, ethylene carbonate, and propylene carbonate, and mixtures thereof.

5. The process of claim 1, wherein the polar solvent is an amide solvent selected from the group consisting of dimethylacetamide, dimethylformamide, N-methylpyrrolidone, dimethylethylenurea, trialkylamines, dimethylpropylenurea, and mixtures thereof.

6. The process of claim 1, wherein the polar organic solvent is nitromethane.

7. The process of claim 1, wherein the polar solvent is acetone nitrile.

8. The process of claim 1, wherein the polar solvent is dimethylsulfoxide.

9. The process of claim 1, wherein the polar solvent is selected from the group consisting of chloropropane, methylene chloride, chloroform, chlorobenzene, and mixtures thereof.

10. The process of claim 1, wherein said solution further contains a catalyst.

11. The process of claim 1, further comprising washing the dialysis membrane with a polar solvent.

12. The process of claim 11, wherein said washing is effective to rinse any residual quantity of a cavity-forming liquid from a hollow-filament cellulosic membrane.

13. An apparatus comprising means for chemically modifying cellulosic dialysis membranes in the form of flat films, tubular films or tubular filaments, including, a piping system which is in communication with at least one storage tank for liquid or gas and with at least one membrane module, and a conveying means to maintain a liquid circulation, wherein the piping system is a ring circuit to which the storage tank is attached through a proportioning device adapted to supply said liquid or gas at a predesignated time and in a predesignated quantity from said storage tank through the ring circuit to said membrane module.

14. The apparatus of claim 13, wherein a plurality of membrane modules are placed in one holding container provided with flow holes and said holding container is placed in a reaction vessel which is interposed in the ring circuit.

15. The apparatus of claim 14, wherein said membrane modules are disposed in said holding container in a close-packed manner.

16. The apparatus of claim 13, further comprising at least 2 storage tanks attached in series through a proportioning device.

17. The apparatus of claim 16, wherein said storage tanks each contain a different member selected from the group consisting of reactants, solvents, and washing agents.

* * * * *